(12) United States Patent
Levy et al.

(10) Patent No.: US 11,033,177 B2
(45) Date of Patent: Jun. 15, 2021

(54) MEDICAL IMAGING DEVICE WITH A TELESCOPIC SCOPE

(71) Applicant: 270 SURGICAL LTD., Netanya (IL)

(72) Inventors: Avraham Levy, Kfar Shmaryahu (IL); Golan Salman, Atlit (IL)

(73) Assignee: 270 SURGICAL LTD., Netanya (IL)

( * ) Notice: Subject to any disclaimer, the term of this patent is extended or adjusted under 35 U.S.C. 154(b) by 0 days.

(21) Appl. No.: 16/464,506

(22) PCT Filed: Oct. 16, 2018

(86) PCT No.: PCT/IL2018/051109
§ 371 (c)(1),
(2) Date: May 28, 2019

(87) PCT Pub. No.: WO2019/077605
PCT Pub. Date: Apr. 25, 2019

(65) Prior Publication Data
US 2020/0113418 A1  Apr. 16, 2020

Related U.S. Application Data

(60) Provisional application No. 62/574,230, filed on Oct. 19, 2017.

(51) Int. Cl.
*A61B 1/00* (2006.01)
*A61B 1/313* (2006.01)

(52) U.S. Cl.
CPC ...... *A61B 1/00066* (2013.01); *A61B 1/00006* (2013.01); *A61B 1/00096* (2013.01); *A61B 1/00135* (2013.01); *A61B 1/3132* (2013.01)

(58) Field of Classification Search
CPC ............ A61B 1/00135; A61B 1/00151; A61B 1/00154; A61B 1/313; A61B 1/3132; A61B 1/3137
See application file for complete search history.

(56) References Cited

U.S. PATENT DOCUMENTS 4,819,620 A  4/1989 Okutsu
6,086,530 A  7/2000 Mack
(Continued)

FOREIGN PATENT DOCUMENTS

CN  105286775  2/2016
EP  0674872  10/1995
(Continued)

OTHER PUBLICATIONS

International Search Report PCT/IL2018/051109 Completed Jan. 23, 2019; dated Jan. 24, 2019 6 pages.
(Continued)

*Primary Examiner* — Alexandra L Newton
(74) *Attorney, Agent, or Firm* — The Roy Gross Law Firm, LLC; Roy Gross

(57) ABSTRACT

The subject matter discloses a medical imaging device, comprising a handle adapted to operate and maneuver the medical imaging device, an elongated rigid shaft connected to the handle, and an extendible sleeve configured to cover at least a portion of the elongated rigid shaft. The extendible sleeve comprises a rigid section comprising at least one optical gear and an extendible section, wherein extending the extendible section pushes the rigid section along a longitudinal axis of the elongated rigid shaft, and wherein sliding the rigid section over the elongated shaft changes the at least one optical gear field of view to provide a different linear field of view in an object space.

6 Claims, 14 Drawing Sheets

(56) References Cited

U.S. PATENT DOCUMENTS

| | | | |
|---|---|---|---|
| 2002/0115908 A1* | 8/2002 | Farkas | G02B 23/2438 |
| | | | 600/178 |
| 2005/0234293 A1* | 10/2005 | Yamamoto | A61B 90/57 |
| | | | 600/102 |
| 2006/0020165 A1 | 1/2006 | Adams | |
| 2007/0112250 A1 | 5/2007 | Kura et al. | |
| 2012/0136213 A1* | 5/2012 | Weimer | G02B 26/0816 |
| | | | 600/173 |
| 2012/0245416 A1* | 9/2012 | Viola | A61B 1/0008 |
| | | | 600/109 |
| 2013/0046137 A1* | 2/2013 | Zhao | A61B 1/00181 |
| | | | 600/102 |
| 2013/0053644 A1 | 2/2013 | Smith et al. | |
| 2013/0282041 A1* | 10/2013 | Gunday | A61B 17/3421 |
| | | | 606/170 |
| 2017/0035276 A1 | 2/2017 | Lombardi et al. | |

FOREIGN PATENT DOCUMENTS

| | | |
|---|---|---|
| EP | 2635932 A2 | 9/2013 |
| EP | 3000422 | 3/2016 |
| WO | 2014053333 | 4/2014 |

OTHER PUBLICATIONS

Written Opinion of the International Searching Authority PCT/IL2018/051109 dated Jan. 24, 2019 6 pages.
European Search Report for EP Application No. 18868639.8 dated Jan. 3, 2020, 7 pp.
Israel Search Report IL266992 dated Jun. 14, 2020, 4 pp.
Article 94(3) EPC communication —EP Application No. 18868639.8 dated Jan. 15, 2020, 7 pp.

* cited by examiner

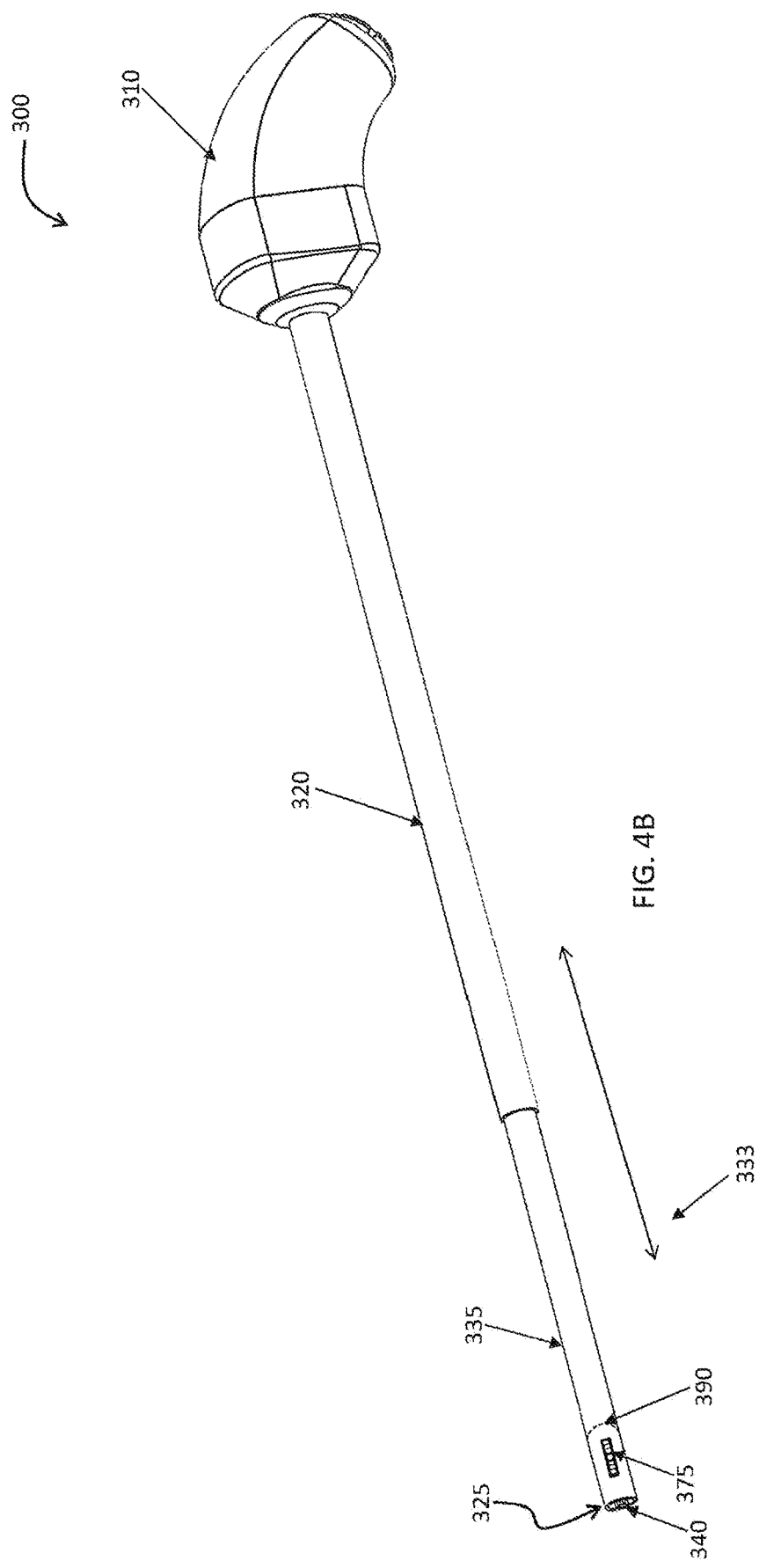

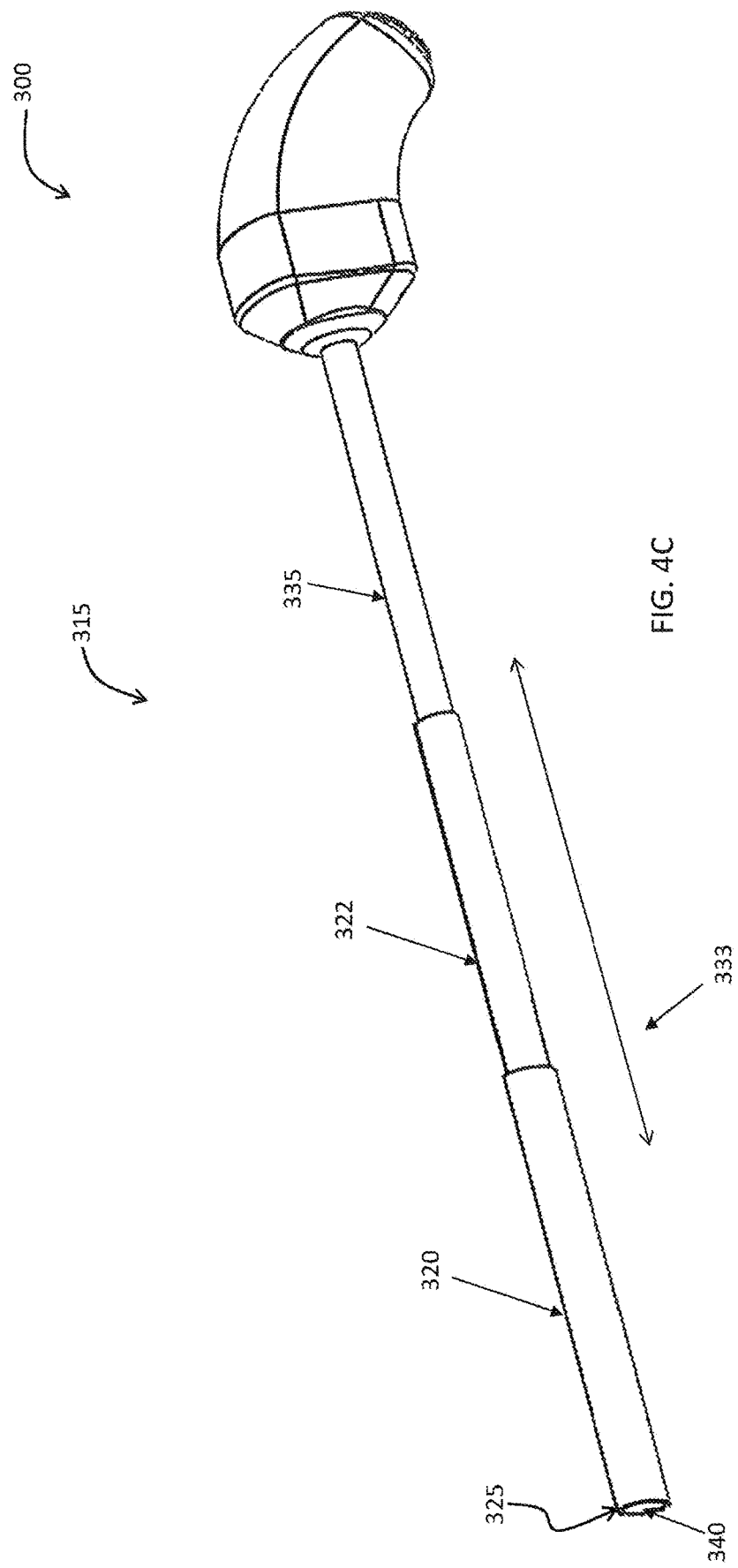

MEDICAL IMAGING DEVICE WITH A TELESCOPIC SCOPE

RELATED APPLICATIONS

This application is a National Phase of PCT Patent Application No. PCT/IL2018/051109 having International filing date of Oct. 16, 2018, which claims the benefit of priority of U.S. Provisional Application No. 62/574,230 filed on Oct. 19, 2017. The contents of the above applications are all incorporated by reference as if fully set forth herein in their entirety.

FIELD OF THE INVENTION

The present invention generally relates to the field of medical instruments designed to capture images from inside the patient's body.

BACKGROUND OF THE INVENTION

A laparoscope and endoscope devices are utilized to perform operations in the internal organs of the body through small entrances in human body. In multiple cases, such operations require the aid of a camera. Furthermore, in some cases, procedures which involve inspection of a region inside confined area or a specific body cavity or organ, may be required to involve more than one camera. As of today, there are multiple different types of endoscopes and laparoscope, depending on the area in which the device is used and the procedure's type. As a result of that, diverse laparoscopes may comprise one or more cameras utilized to capture the field of view of the inspected region.

A standard laparoscope is likely to be assembled in an elongated tubular member in which the lenses and illumination light guide are located. In most cases, the laparoscopes are inserted via a trocar. The device comprises a handle connected to the rigid tube, the handle is held by the person operating the medical procedure. The handle is kept outside the patient's body. In some laparoscopes a camera is located in the handle, in other laparoscopes the camera is located in the distal section of the elongated rigid tube.

SUMMARY OF THE INVENTION

The subject matter disclosed in the present invention discloses a medical imaging device comprising at least two cameras.

It is an object of the subject matter to disclose a medical imaging device, comprising a handle adapted to operate and maneuver the medical imaging device, an elongated rigid shaft connected to the handle, and an extendible sleeve configured to cover at least a portion of the elongated rigid shaft, said extendible sleeve comprises a rigid section comprising at least one optical gear and an extendible section, wherein extending the extendible section pushes the rigid section along a longitudinal axis of the elongated rigid shaft, and wherein sliding the rigid section over the elongated shaft changes the at least one optical gear field of view to provide a different linear field of view in an object space.

In some cases, the extendible section is of accordion like shape. In some cases, the extendible section is in direct contact with the handle. In some cases, the extendible section of the extendible sleeve is made of disposable materials. In some cases, the extendible sleeve covers a distal end of the elongated rigid shaft. In some cases, the medical imaging device further comprises a control unit on the handle, wherein the control unit controls extension and collapse of the extendible section of the extendible sleeve.

In some cases, the extendible section of the sleeve has a collapse state and an extended state, wherein when in extended state, the distal tip of the extendible sleeve is distant from the distal tip of the elongated rigid shaft. In some cases, the at least on optical gear comprises a front optical gear and a side optical gear and electrical circuitry configured to provide power and data to the front optical gear and the side optical gear.

It is an object of the subject matter to disclose a medical imaging device, comprising a handle, and an elongated rigid shaft connected to the handle, comprising at least one optical gear and an extendible section, wherein the handle comprises a channel adapted to an external diameter of the elongated rigid shaft, such that the elongated rigid shaft slides within the channel, wherein sliding the elongated rigid section within the channel changes the at least one optical gear field of view to provide a different linear field of view in an object space.

In some cases, the medical imaging device further comprises a control mechanism connected to the handle, said control unit enables locking and unlocking the shaft inside the channel.

In some cases, the control mechanism is located inside the channel and is detachable to and attachable to the elongated rigid shaft. In some cases, the medical imaging device further comprising a mechanism for moving the shaft in a predefined length according to a medical procedure performed by the device. In some cases, the medical imaging device further comprises a receiver for receiving commands from a central control unit and maneuvering the shaft according to the received commands. In some cases, the rigid shaft has a wire connection to the central control unit, wherein information captured by cameras is transferred to the central control unit through this wire.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4C shows a telescopic shaft, in which sections of the shaft extend farther from the handle, according to exemplary embodiments of the disclosed subject matter; and, FIG. 5 shows a holder for holding and controlling a rigid shaft, according to exemplary embodiments of the disclosed subject matter.

DETAILED DESCRIPTION OF THE INVENTION

The present subject matter discloses a medical imaging device comprising one or more cameras designed to aid medical procedures such as inspection or surgery procedures in the abdomen or pelvis through small incisions. The one or more cameras are mounted on a rigid distal tip connected to a rigid elongated shaft. The shaft is connected to a handle configured to position the shaft, thereby position the one or more cameras. The handle is maneuvered by the user performing the medical procedure either directly or throughout the maneuvering of robotics. The elongated shaft of the present invention is adjustable in length. That is, the user performing the medical procedure may adjust the distance between the one or more cameras and the handle. The adjustment enables extending the range of vision in the patient's body, as the handle remains outside the body. The adjustment also enables keeping the handle in the same place while moving the one or more cameras to another location, according to the procedure's needs, for example when there is a need to affix the handle. The adjustment may be implemented by sliding the shaft into a niche in the handle, or using a sleeve (either internal or external to the elongated rigid shaft).

In some cases, such a medical imaging device can be utilized in laparoscopy wherein the medical imaging device can be put through an incision in the body in order to perform medical procedures at the internal organs. In some embodiments of the disclosed subject matter the medical imaging device disclosed herein can comprise two section members directly connected. Said two section members may be an elongated rigid shaft tube and a distal tip. The distal tip can comprise the optical gear required for the medical procedures, and in some cases, be mounted directly on the rigid shaft. In some cases, the optical gear located in the distal tip can comprise sensor, lenses (e.g., camera) and light sources required for the sensor functioning.

Figure 1:
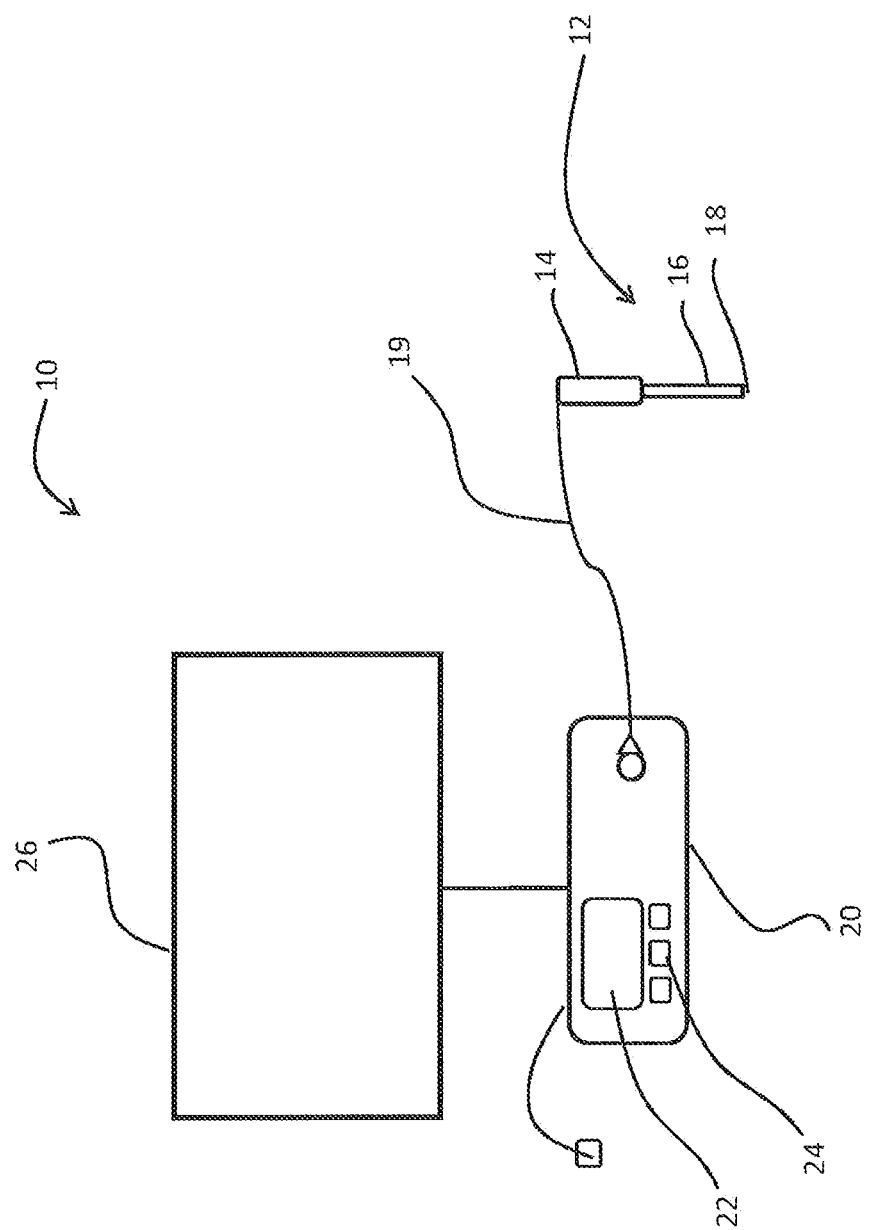
FIG. 1 illustrates a multiple camera rigid scope system, according to exemplary embodiments of the disclosed subject matter.

FIG. 1 shows a multiple camera rigid scope system, according to exemplary embodiments of the disclosed subject matter. System 10 may include a multi camera rigid endoscope 12. Multi camera rigid endoscope 12 may include a handle 14, connected to an elongated rigid shaft 16. Elongated rigid shaft 16 terminates with a distal tip section 18. Handle 14 may be used for guiding elongated rigid shaft 16 within a body cavity. Handle 14 may include one or more buttons and/or switches (not shown) configured to enable a user of the system 100 to control functions such as zoom, focus and elongated movement of rigid shaft 16.

A utility cable 19, may connect between handle 14 and a main control unit 20. Utility cable 19 may include therein one or more electrical channels. The electrical channel(s) may include at least one data cable for receiving video signals from a front and at least one side cameras, as well as at least one power cable for providing electrical power to the cameras and to the illuminators. In another embodiment, wireless communication between handle 14 and main control unit 20 is used.

Main control unit 20 contains the controls required for displaying the images of internal organs captured by the rigid scope cameras. Main control unit 20 may provide or control power transmission to the endoscope's distal tip components, such as for the cameras and illuminators. One or more input devices, such as a keyboard, a mouse, a touch screen and the like may be connected to the main control unit 20 for the purpose of controlling the main control unit 20. In the embodiment shown, the main control unit 20 comprises a control screen 22 for displaying operation information concerning the operation of the rigid endoscope 12. The operation information may be changed and/or determined by operation buttons 24 of the main control unit 20.

An image monitor 26 may be configured to display images and/or video streams received from the cameras of the rigid endoscope 12. Monitor 26 may further be operative to display a user interface for allowing a user to set various features of the endoscopy system 10.

The images/videos may be displayed separately on one or more monitors by uploading information from main control unit 20, either side-by-side or interchangeably (namely, the user may switch between views from the different viewing elements manually). Alternatively, these video streams may be processed by main control unit 20 to combine them into a stitched image based on an overlap between fields of view of the cameras.

FIGS. 2A-2F demonstrates a medical imaging device with a moving elongated rigid shaft, according to exemplary embodiments of the disclosed subject matter. The medical imaging device 100 comprises a handle 110 connected to the elongated rigid shaft 120. The elongated rigid shaft 120 comprises one or more cameras positioned at a distal tip 125 of elongated rigid shaft 120. In another embodiment, elongated rigid shaft 120 comprises multiple cameras, while at least one of the multiple cameras is a front camera positioned at a distal tip 125 of the elongated rigid shaft 120. The elongated rigid shaft 120 may also comprise one side camera, or multiple side cameras, which provide additional view to the user performing the medical procedure. The rigid shaft 120 has a constant length, for example in the range of 100-700 millimeters. In the embodiments disclosed in FIGS. 2A-2F, without any extension such as sleeve that slide on the shaft 120, a shaft's length L is the maximal distance between a front panel 135 of the distal tip 125 and the handle 110.

Figure 2A:
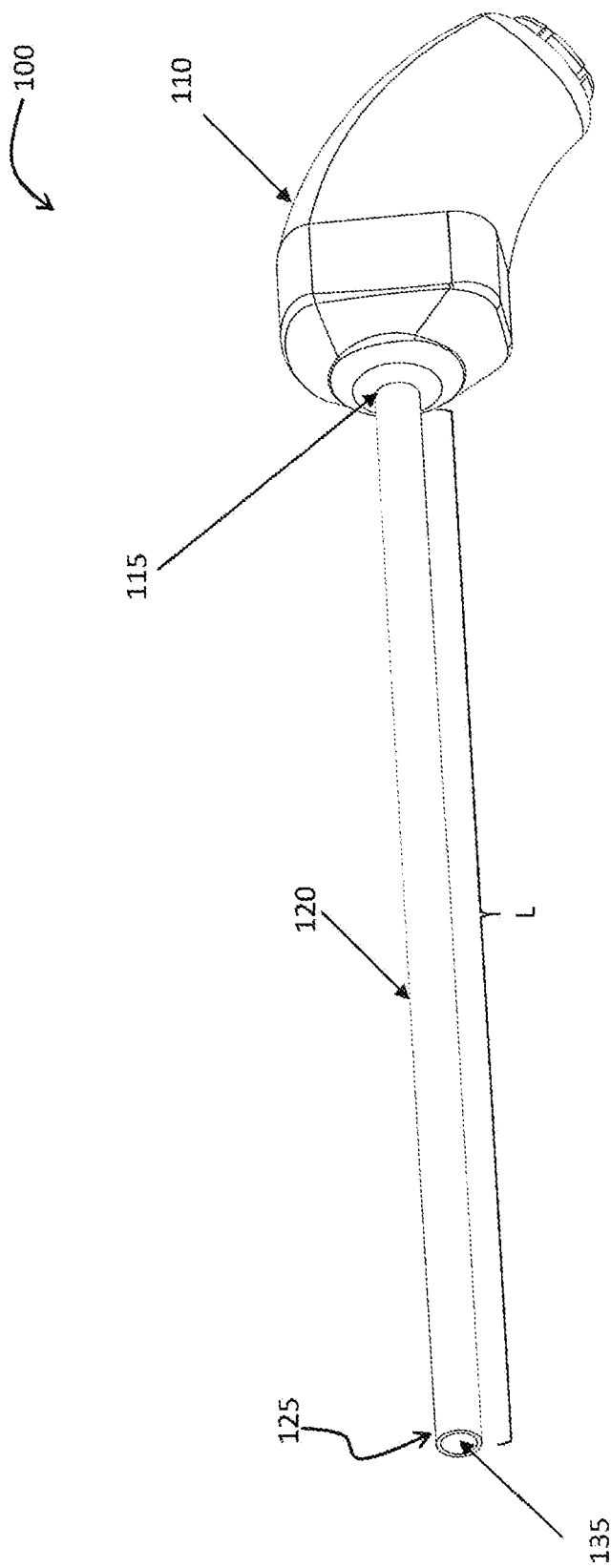
FIGS. 2A-2F demonstrates a medical imaging device with a moving elongated rigid shaft, according to exemplary embodiments of the disclosed subject matter.
Figure 2B:
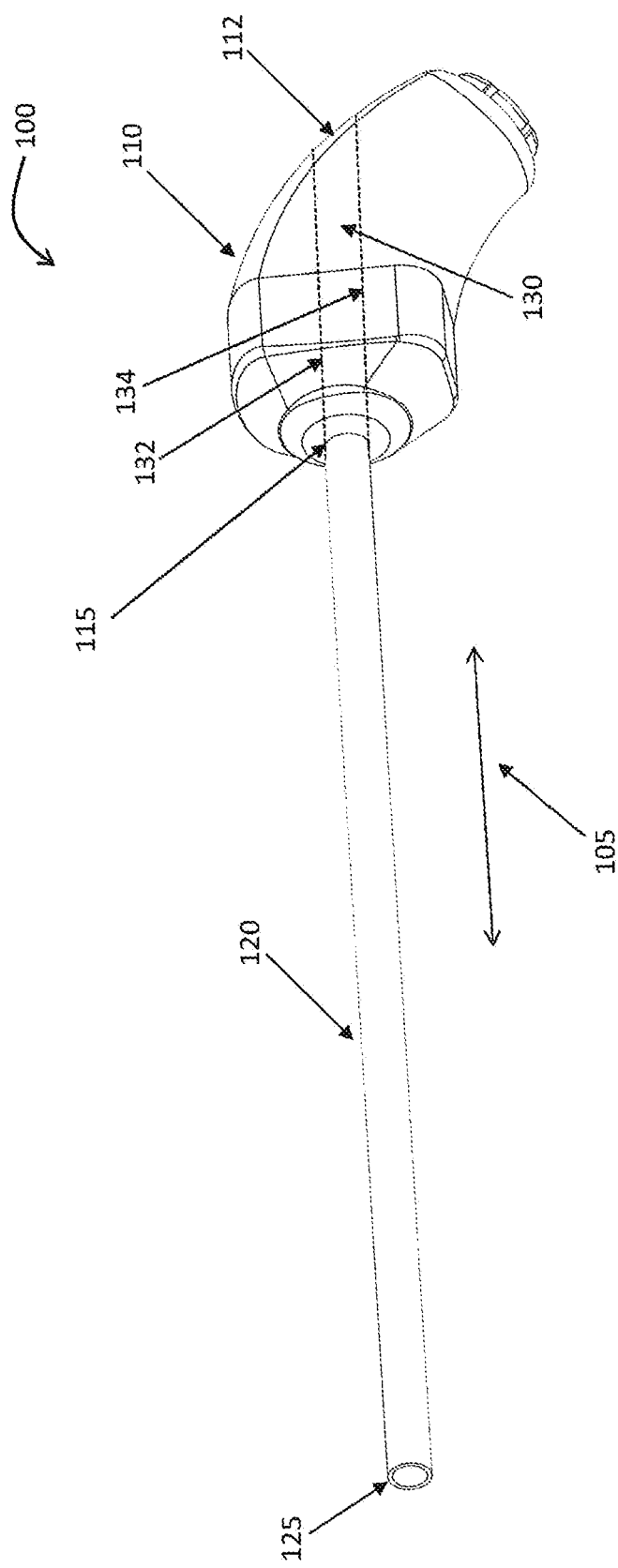

The handle 110 has an opening 115 in which the shaft 120 enters the handle when moved backwards, towards the handle 110. The shaft 120 moves along its longitudinal axis 105. In some embodiments, the shaft's movement is limited to the length of the handle 110, and the shaft cannot exit in the rear side of the handle, outside the patient's body. In some other cases, as shown in FIGS. 2D-2F, the shaft 120 slides along a channel 130 located within the handle 110 and exits at the rear opening 112 of the handle 110, which enables a larger adjustment range of the shaft 120. The larger adjustment range of the shaft 120 also provides a larger positioning range of the cameras within the shaft 120, as the cameras do not move along the shaft 120.

The elongated rigid shaft 120 slides into channel 130 in the handle 110 via opening 115. The channel 130 may have substantially the same shape and size as the elongated rigid shaft 120. For example, the shaft 120 may have a circular cross section with a diameter of 10 millimeters and the channel 130 may also have a circular cross section with a diameter in the range of 10.1-11.5 millimeters. In another example, shaft 120 may have a circular cross section with a diameter of 2.5 millimeters and channel 130 may also have a circular cross section with a diameter in the range of 2.4-3.0 millimeters. The circular cross section enables the shaft 120 to slide within channel 130 without changing the orientation of shaft 120 relatively to a region of interest, yet changing the distance of shaft 120 from the region of interest during the medical procedure. The change of distance enables the user to change the linear field of view in an object space without changing the position and location of handle 110. In another embodiment, rotating the shaft 120 while inserted into the channel 130 changes the distance of shaft 120 and the linear field of view from the region of interest during the medical procedure without changing the position and location of handle 110. In some embodiments, the channel's cross section may be polygonal. For simplicity, FIG. 2B shows the topmost inner wall 132 of the channel 130 and the bottom point 134 of the channel 130.

Figure 2C:
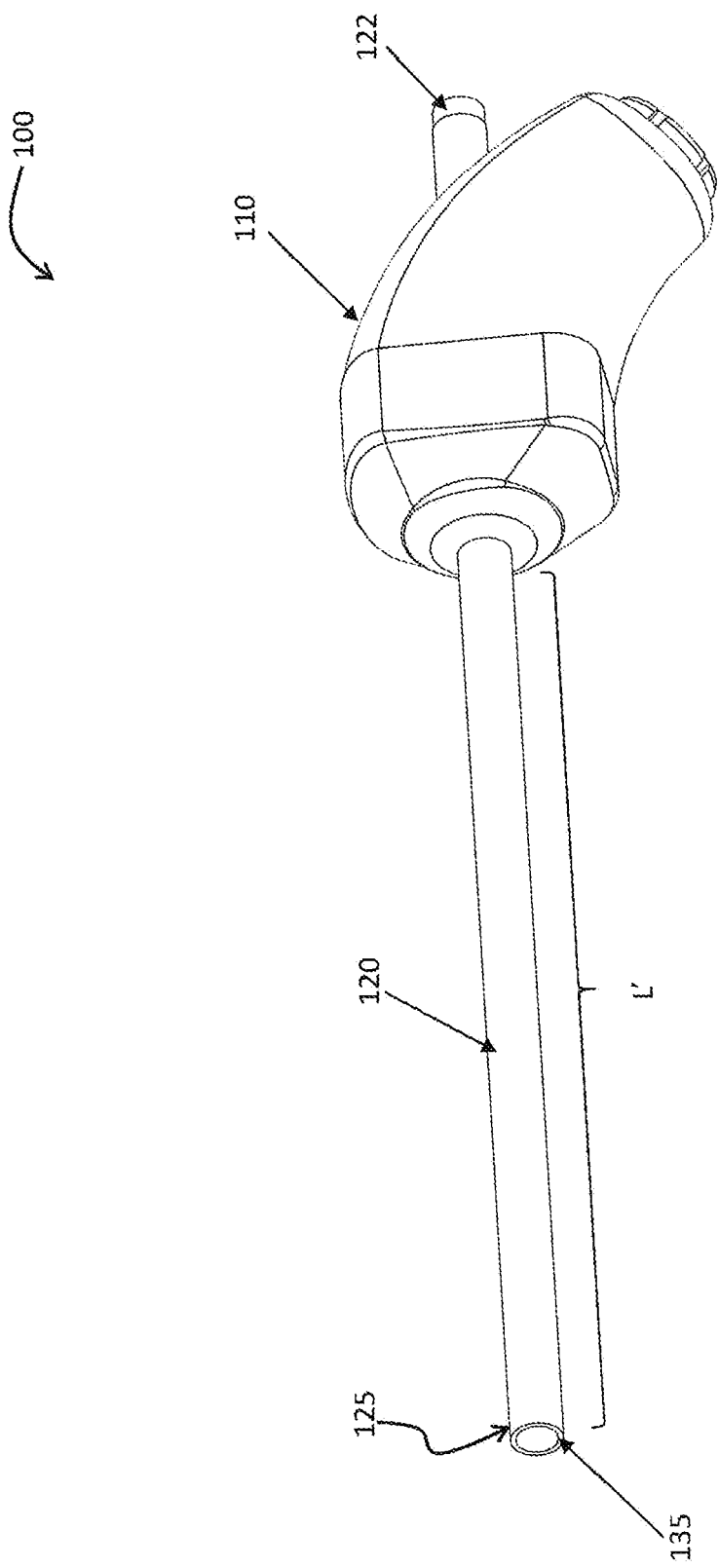
Figure 2D:
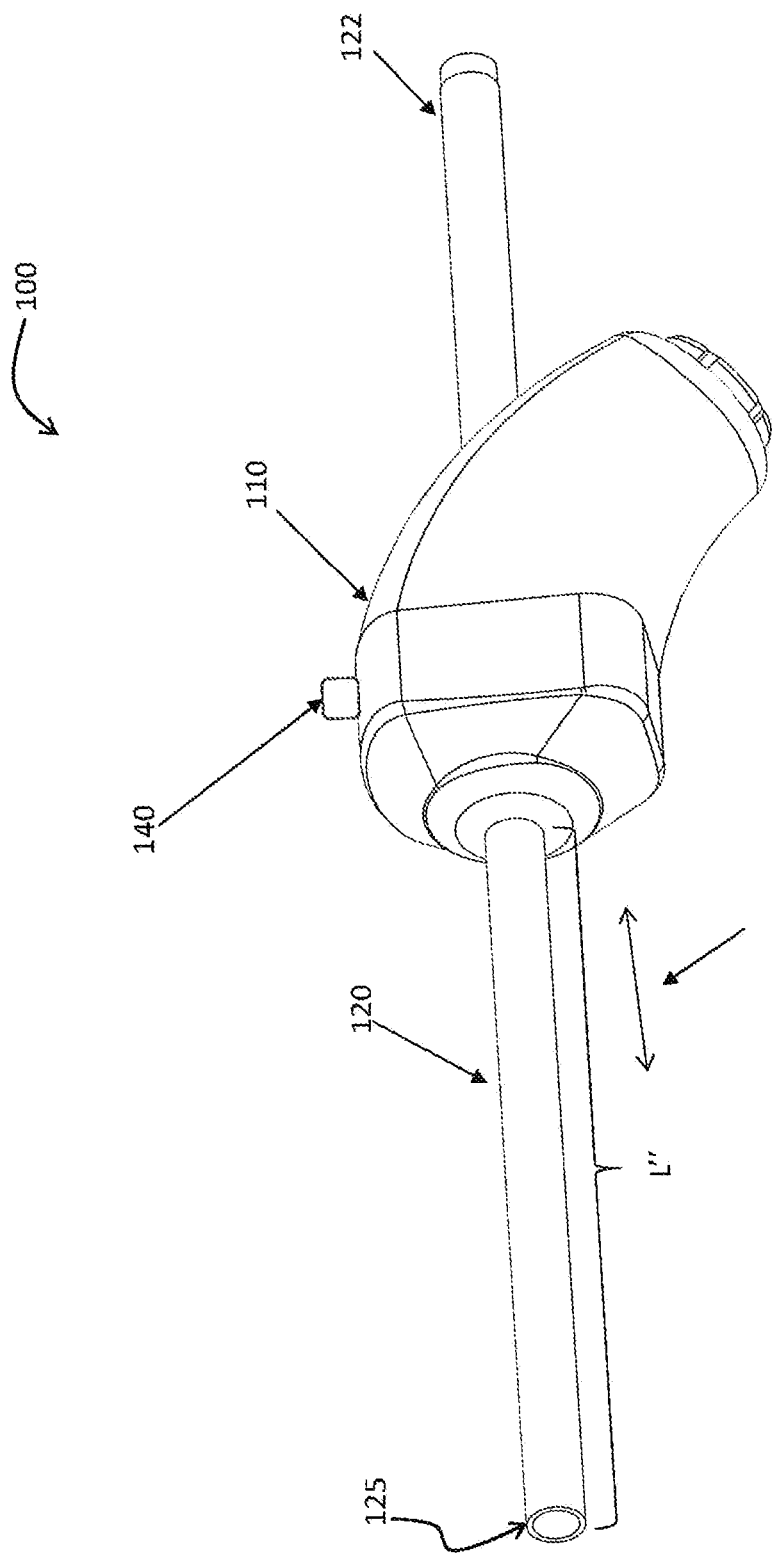
Figure 2E:
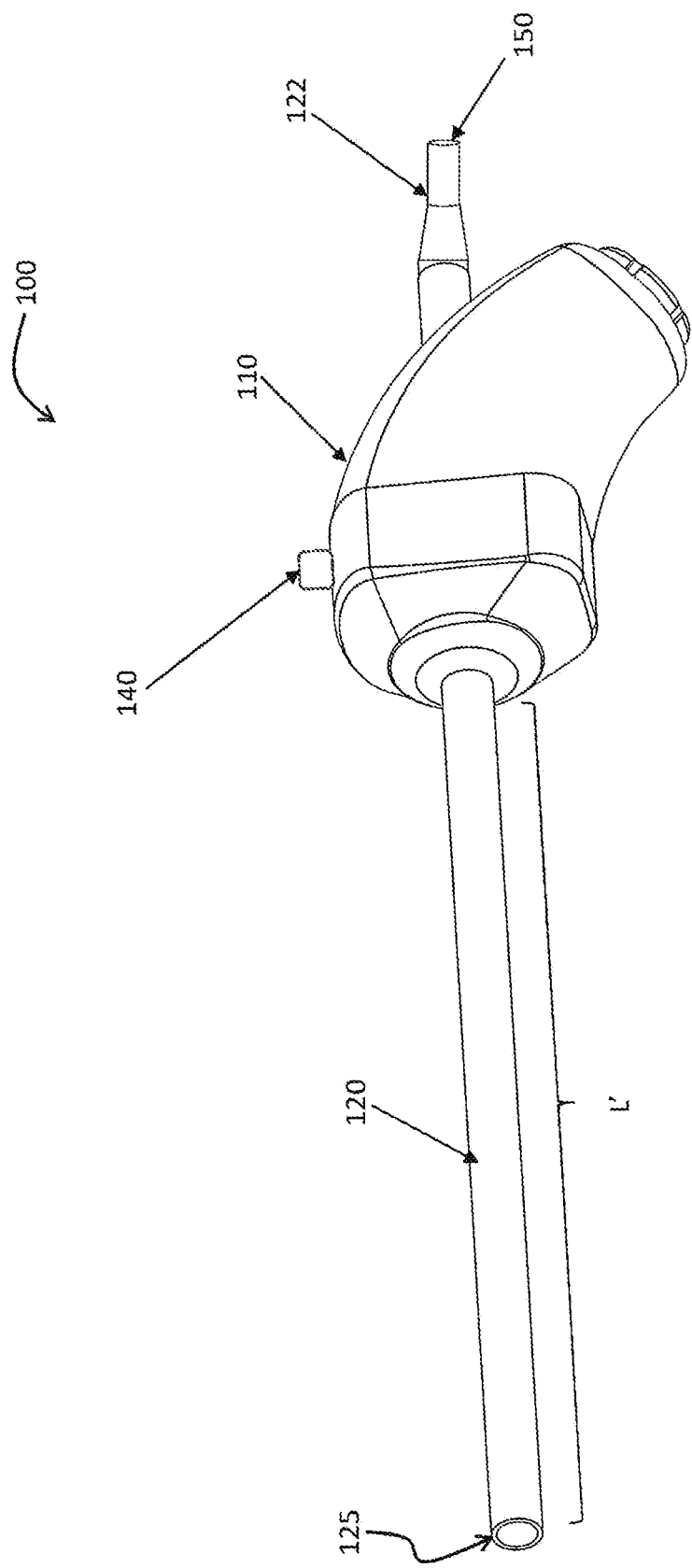
Figure 2F:
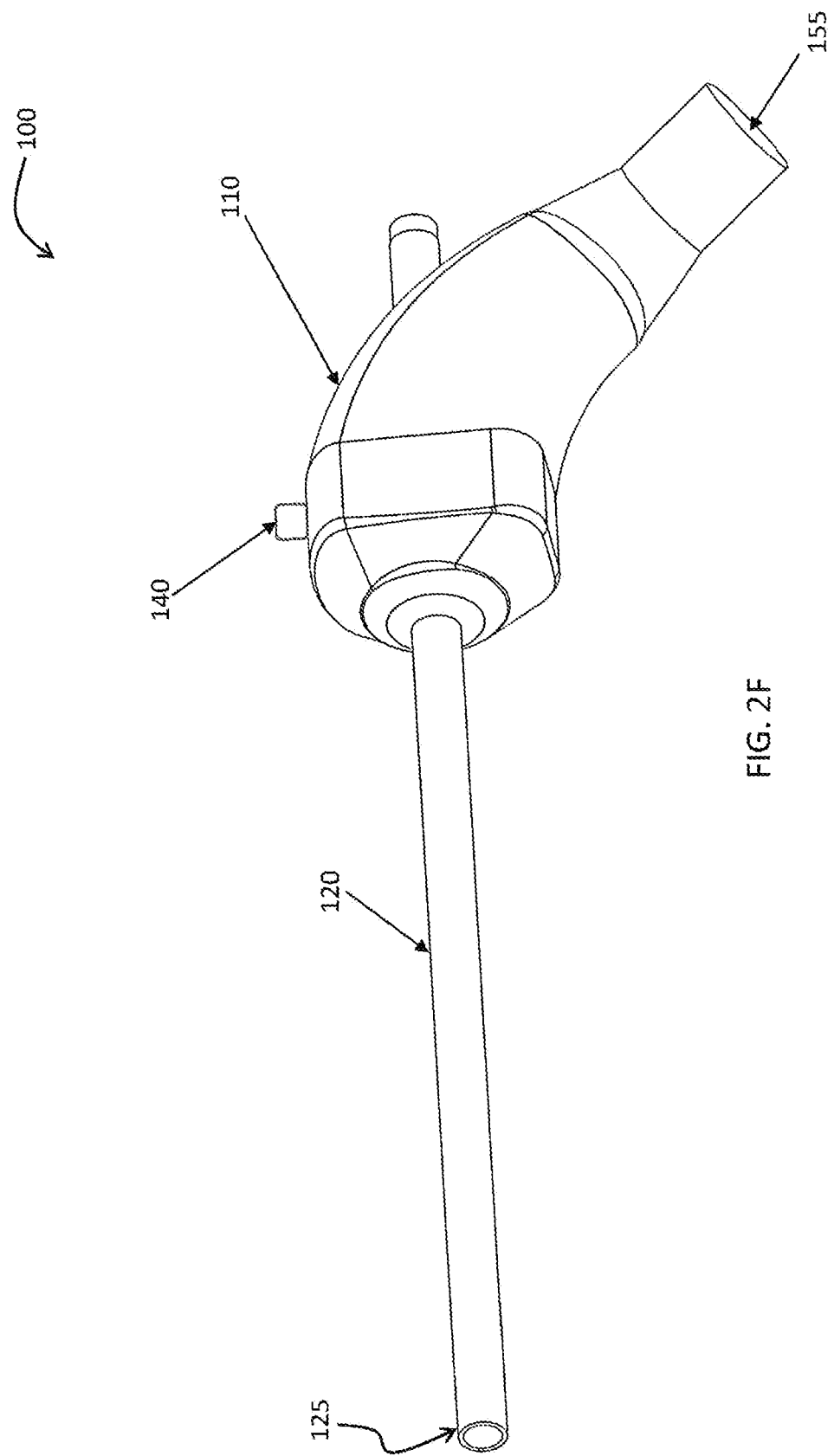

FIG. 2C shows a proximal end 122 of the rigid elongated shaft 120 after exiting from the channel 130, and FIG. 2D shows the rigid elongated shaft 120 moved farther to the rearward direction. The length L', defined between front panel 135 of distal tip 125 and the handle 110, is smaller than the maximal length L of the elongated rigid shaft 120. For example, the difference between the maximal length L and the length L' may be in the range of 0.5-30 millimeters. The length L", defined between front panel 135 of distal tip 125 and the handle 110, is smaller than the maximal length L' of the elongated rigid shaft 120. For example, the difference between the maximal length L' and the length L" may be in the range of 0.5-25 millimeters.

In some embodiments, the rigid shaft 120 comprises markings such as a slide rule comprising scale intervals enable determination of the length of rigid shaft 120 from front panel 135 of distal tip 125 to the handle 110.

In an embodiment, the device 100 may have a predefined maximal adjustability distance. For example, in an embodiment the length L of rigid shaft 120 may indicate 30 mm for maximum length L of rigid shaft 120, length L' of rigid shaft 120 indicating 20 mm shows the user of the device 100 that shaft 120 has moved rearwards by 10 mm.

In some other embodiments, a mechanical element may be used to provide an indication of how far the shaft 120 moved along its longitudinal axis 105. Such mechanism may include a tooth extending from the internal wall of channel 130.

FIG. 2E shows an electronic connector 150 connected to or embedded in the proximal end 122 of the rigid elongated shaft 120. The electronic connector 150 enables data transfer from the device 100 to a central system, such as main control unit 20 of FIG. 1, that displays the images captured by the cameras of the device 100, such as display 26 of FIG. 1. The central system may also process the images before display. In some other embodiments, the images are transferred from the cameras located within distal tip 125 of rigid shaft 120 to the central system (not shown) using wireless communication. In such a case, the shaft comprises a wireless transmitter. FIG. 2F shows an electronic connector 155 connected to or embedded in the handle 110 enables wireless transmitter between handle 110 and shaft 120.

In some embodiments, the device 100 also comprises a knob 140 enabling the user operating the medical procedure to regulate the shaft's movement. For example, the knob 140 may have an internal section within the channel 130. In such case, when the knob 140 is in downward position, the internal section presses the shaft 120 and locks the shaft 120 in a specific position. When the user touches or moves the knob 140, it unlocks the shaft 120 and enables pulling the shaft 120 rearward or forward. For example, the knob 140 may be attached to a spring (not shown) attached to the bottom point 134 of the channel 130 and securing the shaft 120 upwards. This way, when the user operating the device 100 presses down the knob 140, the spring shrinks and the shaft loosens and is free to move. In this specific embodiment, the user locks the shaft 120 by moving the knob 140 upwards.

Once the shaft 120 is moved by the user, the shaft 120 is affixed in its new position. Such fixation may be achieved by friction between the external surface of the shaft 120 and the inner walls of the channel 130 to lock the shaft 120 in place. Other mechanisms may be used to regulate the shaft's movement rearward and forward.

Figure 3A:
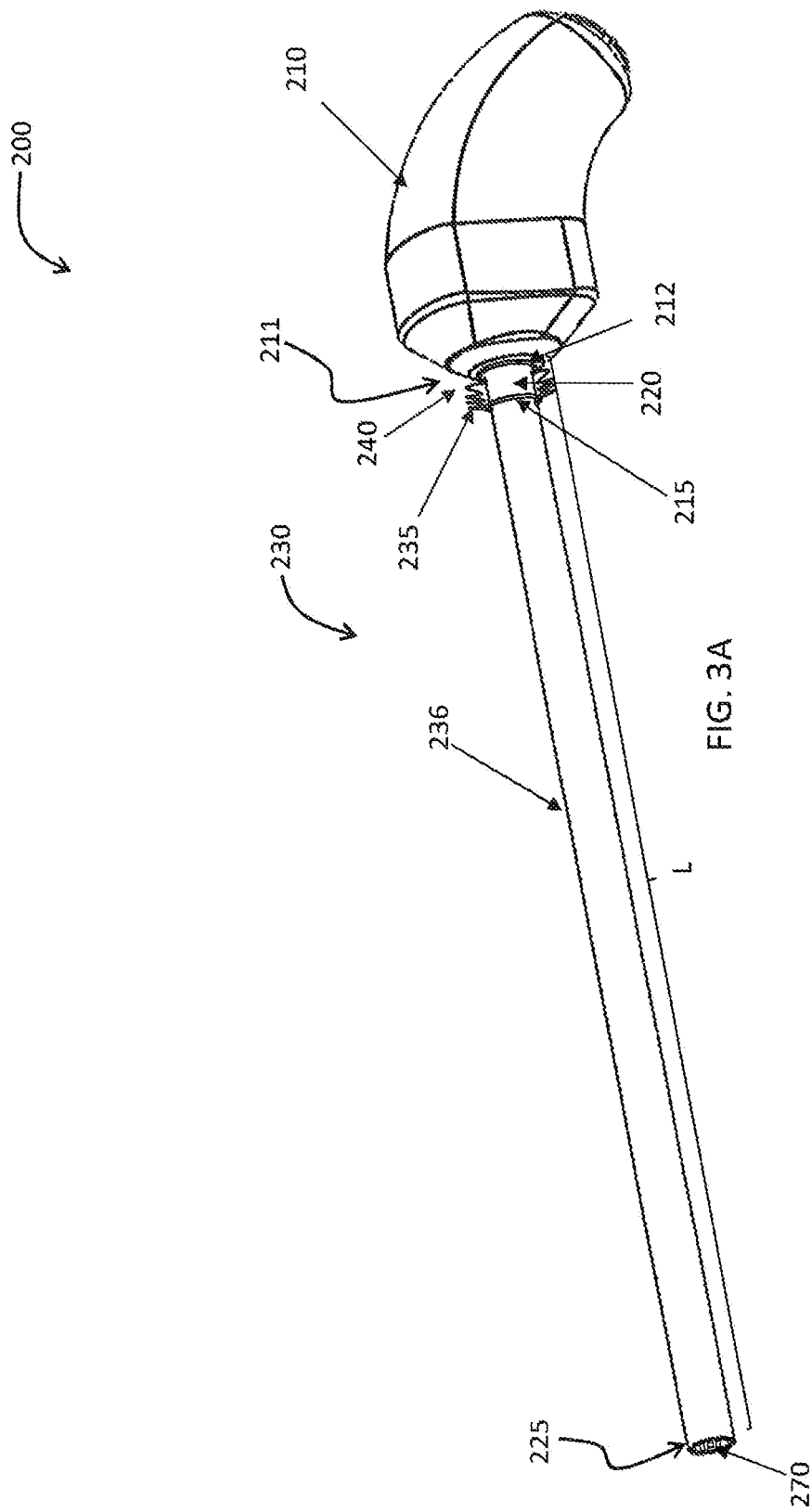
FIGS. 3A-3C demonstrates a medical imaging device comprising an extendible sleeve for extending a rigid shaft of the medical imaging device, according to exemplary embodiments of the disclosed subject matter.
Figure 3B:
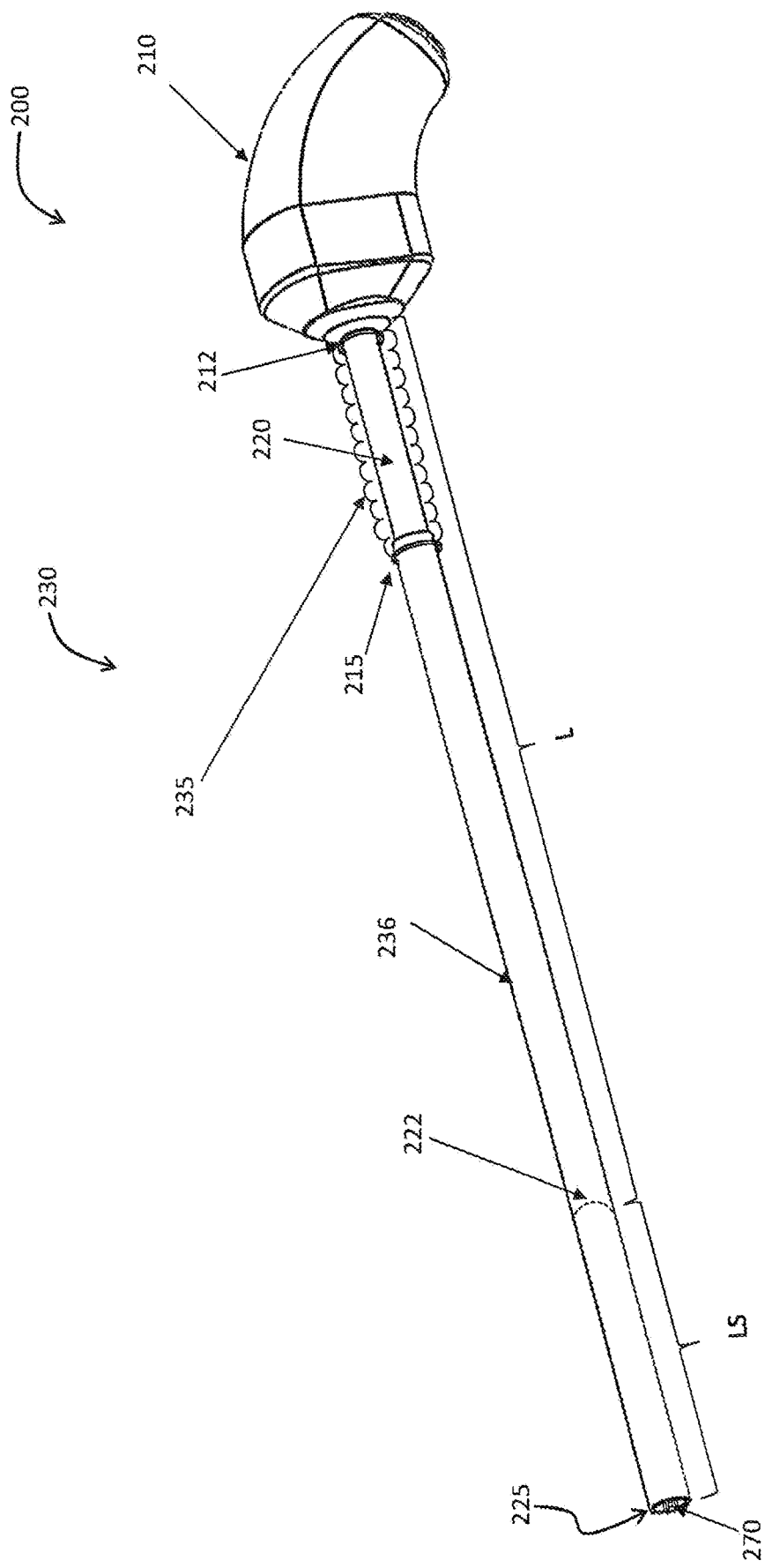
Figure 3C:
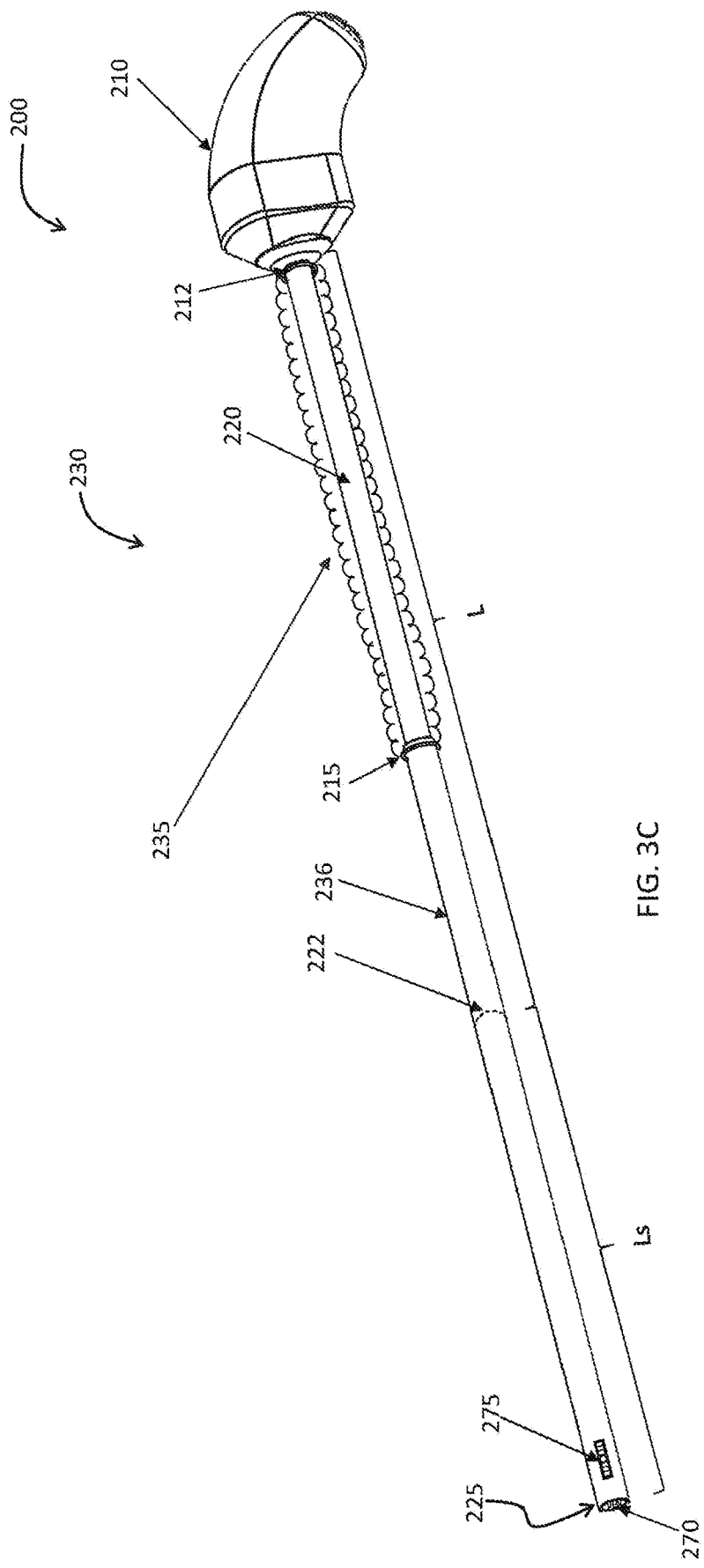

FIGS. 3A-3C illustrates another medical imaging device comprising an extendible sleeve for extending a rigid shaft of the medical imaging device, according to exemplary embodiments of the disclosed subject matter. The extendible sleeve may be sustainable, for example made of a reusable material, or disposable, for example made of a material such as plastics, paper, polymer and the like. An optical gear (including a lens assembly or assemblies (lenses and sensor) and illuminators) may be found either on a distal tip of the extendible sleeve or on a distal tip of the rigid shaft. In some embodiments, the extendible sleeve comprises a distal rigid section located farther than the handle and an extendible part. The distal rigid section may be made of metal, for example made of stainless steel.

FIG. 3A shows a medical imaging device 200 configured to be inserted into the patient's body. The medical imaging device 200 comprises a handle 210 allowing a user to operate and maneuver the medical device. An elongated rigid shaft 220 is connected to the handle 210, for example at a front end 211 of the handle 210. An extendible sleeve 230 covers the elongated rigid shaft 220, or a portion thereof. In some exemplary cases, as shown in FIG. 3A, the extendible sleeve 230 covers the entire elongated rigid shaft 220, as the extendible sleeve 230 is in direct contact with the handle 210. In some other cases, the extendible sleeve 230 surrounds only a portion of the elongated rigid shaft 220. The extendible sleeve 230 has an extendible section 235 defined between a proximal connector 212 and a distal connector 215. The proximal connector 212 may be positioned at the connection point 240 between the elongated shaft 220 and the handle 210. In some other embodiments, the proximal connector 212 may be positioned on the shaft 220. In some other embodiments, the proximal connector 212 may be affixed to a distal surface of the front end 211 of handle 210. The proximal connector 212 and the distal connector 215 may be defined as rings surrounding the shaft 220. The connectors 212 and 215 may be hinges or hooks connected to a static location on the medical imaging device 200. According to some embodiments, proximal connector 212 and distal connector 215 adapted to seal elongated rigid shaft 220 and handle 210 such as to essentially prevent entry of fluids from the environment of the medical procedure to inner parts of medical imaging device 200.

The extendible sleeve 230 also comprises a rigid section 236 which moves farther from the handle 210 when the extendible section 235 extends. Thus, when the extendible section 235 is in collapse position, as shown in FIG. 3A, a distal tip 225 of the extendible sleeve 230 may be in the area of the distal tip of the shaft 220, such an overlap is found between the distal tip 225 of extendible sleeve 230 and a distal tip (not shown) of elongated shaft 220. When the extendible section 235 is in extended position, as shown in FIG. 3B, the distal tip 225 of the extendible sleeve 230 is distant from the distal tip 222 of the elongated shaft 220. The distance LS between the distal tip 225 of the extendible sleeve 230 and the distal tip 222 of the shaft 220 depends on how much the extendible section 235 extends. In some exemplary cases, the user performing the medical procedure may extend the extendible section 235 according to the medical needs. Extending the extendible section 235 may be done manually by pulling or pushing the extendible section 235 farther from the handle 210. The extendible section 235 may be rigid or semi rigid in the shape of an accordion, in which the members collapse one above the other when in collapse position, and one next to the other when in extended position. In some embodiments, the extendible section 235 is elastic and loose in the collapse position. The rigid extendible section 236 may be made of plastics, cardboard, thickened fabric, metal, for example made of stainless steel and the like. FIG. 3C shows the extendible sleeve 230 in its longest extension, in which the distance LS is the maximal distance enabled by extending the extendible section 235 of extendible sleeve 230.

The medical imaging device 200 of the present invention further comprises an actuating mechanism for maneuvering extending the extendible section 235 by moving the distal connector 215 farther from the proximal connector. The actuation mechanism may comprise a micro motor attached to the distal connector 215. The micro motor is controlled by the user operating the medical imaging device 200. For example, the handle 210 may comprise a control unit controlled by the user, for example a knob attached to the proximal or upper surface of the handle 210. The control unit is connected to a transmitter that transmits signals to the micro motor of the distal connector 215. Thus, when the user wishes to extend or shorten the distance between the cameras and the handle 210, the user maneuvers or touches the control unit and the distal connector 215 moves according to the user's input into the control unit.

In some other embodiments, the distal connector 215 may be connected to a piston controlled by the control unit, or to another mechanism such as a roller. When using the roller or piston, there is no need for the transmitter and the micro motor attached to the distal connector 215, and the roller or piston are maneuvered from the handle 210.

Rigid extendible section 236 of extendable sleeve 230 further comprises on its distal tip 225 at least one optical gear required for the medical procedures. In some cases, the optical gear located in the distal tip 225 can comprise sensor, lenses (e.g., camera) and light sources required for the sensor functioning. In an embodiment, at least one optical gear is placed on a front panel of distal tip 225 at least one front optical gear 270 is adapted to provide a front field of view for imaging device 200. In some embodiments, further to the at least on front optical gear 270 at least one first side optical gear 275 is placed on the longitudinal side of distal tip 225 adapted to provide a side field of view for imaging device 200. In another embodiment, distal tip 225 may comprise at least one second side camera located at the opposite side of the at least one first side optical gear.

Extendible section 235 of extendable sleeve 230 enables rigid extendible section 236 to slide over shaft 220 without changing the orientation of elongated shaft 220 relatively to a region of interest, yet changing the distance of elongated shaft 220 from the region of interest during the medical procedure. Changing said distance enables to change the linear field of view in the object space without changing the position and location of medical imaging device 200.

Figure 4A:
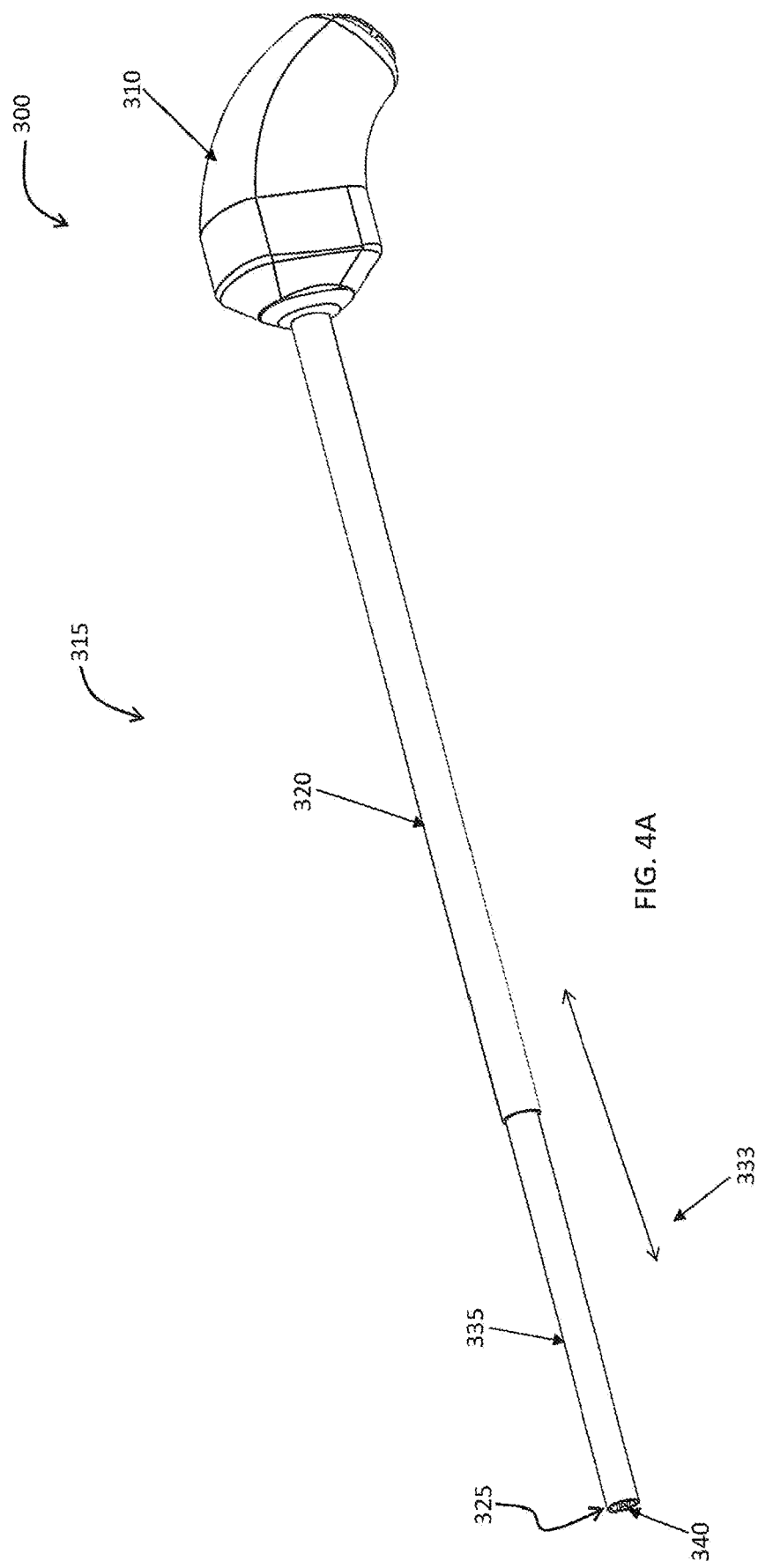

FIGS. 4A-4C show a telescopic shaft, in which sections of the shaft extend farther from the handle, according to exemplary embodiments of the disclosed subject matter. An inner shaft section 335 is located inside an outer rigid shaft section 320 of a rigid elongated shaft 315. Outer rigid shaft section 320 can be provided with a diameter between 2.5 to 20.0 millimeters and inner shaft section 335 may have a predefined adjustability diameter fit to slide within outer rigid shaft section 320. For example, in an exemplary embodiment the diameter of inner shaft section 335 may range between 2.4 to 19.9 millimeters. The inner shaft section 335 extends on the longitudinal axis 333 of rigid elongated shaft 315. Inner shaft section 335 comprises a distal tip connected at a distal end of inner shaft section 335. It should be noted that in some embodiments, two or more sections extend from the outer rigid shaft section 320. For example, first section extends from the outer rigid shaft section 320, and a second section extends from the first section.

Distal tip 325 of inner shaft section 335 further comprises at least one optical gear required for the medical procedures. In some cases, the optical gear located in the distal tip 325 can comprise sensor, lenses (e.g., camera) and light sources required for the sensor functioning. In an embodiment, at least one optical gear is placed on a front panel of distal tip 325. At least one front optical gear 370 is adapted to provide a front field of view for a medical imaging device 300.

According to some embodiments, distal tip 325 may further comprise at least one first side optical gear 375 placed on the longitudinal side of distal tip 325 adapted to provide a side field of view for medical imaging device 300. In another embodiments, distal tip 325 may comprise at least one second side optical gear (not shown) located at the opposite side of the at least one first side optical gear 375.

Inner shaft section 335 is configured to fully slide within outer rigid shaft section 320 such that at least one side camera may be covered by outer rigid shaft section 320. In order to indicate a user of reaching proximity to side optical gear of distal tip 325, an indicator 390 may be placed, as shown in FIG. 4B. For example, indicator 390 may be a groove, a bump a tooth and the like.

In contrast to the first embodiment depicted in FIGS. 4A-4B, in the embodiment depicted in FIG. 4C, inner shaft section 335 may be connected to handle 310 as outer rigid shaft section 320 slides over inner shaft section 335 along longitudinal axis 333 of rigid elongated shaft 315. It should be noted that in some embodiments, two or more sections extend from the outer rigid shaft section 320. For example, FIG. 4C shows a first section 322 that extends from inner shaft section 335, and a second section 320 extends from first section 322. Outer rigid shaft section 320 comprises a distal tip 325 connected at a distal end of outer rigid shaft section 320. Distal tip 325 further comprises at least one optical gear required for the medical procedures. In some cases, the optical gear located in the distal tip 325 can comprise sensor, lenses (e.g., camera) and light sources required for the sensor functioning. In an embodiment, at least one optical gear is placed on a front panel of distal tip 325. At least one front optical gear 370 is adapted to provide a front field of view for a medical imaging device 300

Distal tip 325 may further comprise at least one first side optical gear placed on the longitudinal side of distal tip 325 adapted to provide a side field of view for medical imaging device 300 optionally, distal tip 325 may comprise at least one second side optical gear located at the opposite side of the at least one first side optical gear.

Figure 5:
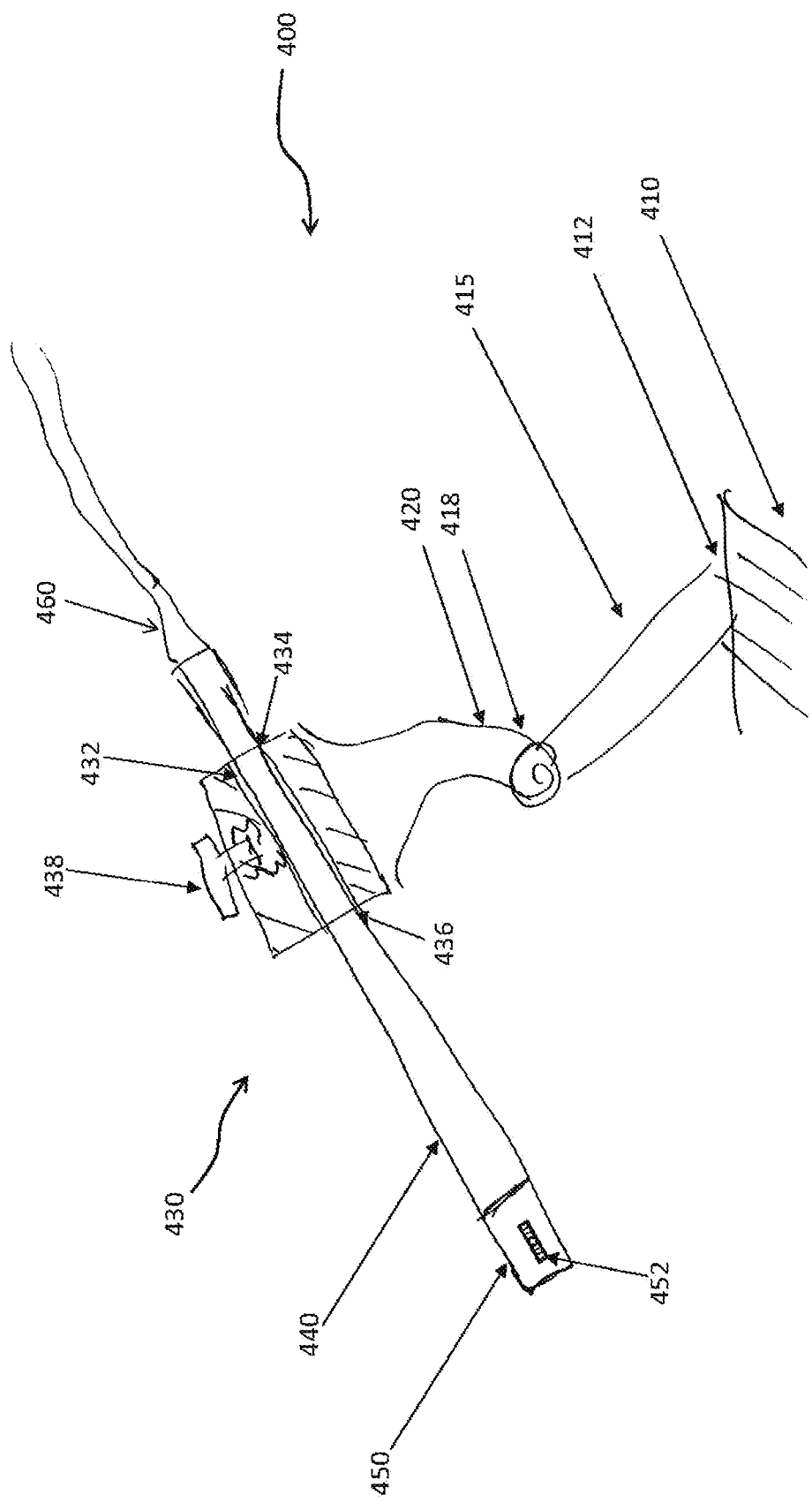

FIG. 5 shows a holder for holding and controlling a rigid shaft, according to exemplary embodiments of the disclosed subject matter. The holder may be placed outside the patient's body, for example anchored to patient's bed, stabilized device, robotics and the like. The holder is mounted on a surface 410, for example a floor, the patient's bed, stabilized device, robotics and the like. The holder comprises one or more limbs connected to a pivot 418 to allow various height and penetration angles towards the patient's body. Basic limb 415 is connected to a base 412 mounted on the surface 410. The base 412 is used to stabilize the device 400. The device 400 comprises a second limb 420 connected on one end to the pivot 418 and on another end to a holder body 430. The holder body 430 comprises a channel 432, used to enable movement of an elongated rigid shaft 440 therein. Channel 432 has two openings at each end, proximal opening 434 and distal opening 436, both adapted to enable sliding of elongated shaft 440 in and out of holder body 430. Channel 432 may have a predefined adjustability diameter fit for elongated rigid shaft 440 to slide within. For example, elongated rigid shaft 440 may have a circular cross section with a diameter of 10 millimeters and the channel 432 may also have a circular cross section with a diameter in the range of 10.1-11.5 millimeters. In another example, elongated rigid shaft 440 may have a circular cross section with a diameter of 5 millimeters and channel 432 may also have a circular cross section with a diameter in the range of 5.1 to 6.5 millimeters. In another example, elongated rigid shaft 440 may have a circular cross section with a diameter of 2.5 millimeters and channel 432 may also have a circular cross section with a diameter in the range of 2.6 to 3.1 millimeters.

Channel 432 enables elongated rigid shaft 440 to slide within without changing the orientation of elongated rigid shaft 440 relatively to a region of interest, yet changing the distance of elongated rigid shaft 440 from the region of interest during the medical procedure which enables the user to change the linear field of view in the object space without changing the position and location of holder body 430. In some embodiments, elongated rigid shaft 440 diameter varied between 2.5 to 20 mm such that channel 432 of device 400 is adapted to hold, grip and slide such diameters.

In some embodiments, holder body also comprises a locking mechanism 438 enabling the user operating the medical procedure to regulate elongated rigid shaft 440 movement. For example, locking mechanism 438, such as a screw, a knob, a button and the like, may have an internal section within channel 432. In such case, when locking mechanism 438 is in locking position, the internal section presses elongated rigid shaft 440 and locks elongated rigid shaft 440 in a specific position. When the user touches or moves locking mechanism 438, it unlocks elongated rigid shaft 440 and enables pulling elongated rigid shaft 440 rearward or forward.

Once the elongated rigid shaft 440 is moved by the user it is affixed in its new position. Such fixation may be achieved by friction between the external surface of elongated rigid shaft 440 and the inner walls of the channel 432 to lock elongated rigid shaft 440 in place. Other mechanisms may be used to regulate the shaft's movement rearward and forward.

Distal tip 450 of elongated rigid shaft 440 further comprises at least one optical gear required for the medical procedures. In some cases, the optical gear located in the distal tip can comprise sensor, lenses (e.g., camera) and light sources required for the sensor functioning. In an embodiment, at least one optical gear is placed on a front panel of distal tip 450. At least one front optical gear (not shown) is adapted to provide a front field of view for a medical imaging device 400.

According to some embodiments, distal tip 450 may further comprise at least one first side optical gear 452 placed on the longitudinal side of distal tip 450 adapted to provide a side field of view for medical imaging device 400. In another embodiments, distal tip 450 may comprise at least one second side optical gear (not shown) located at the opposite side of the at least one first side optical gear 452.

Electrical cables 460 carrying information extracted from the cameras may be connected to the proximal end of elongated rigid shaft 440. The optical gears located at the distal end 450 transfer information via the rigid shaft 440 to the electrical cables 460. In some embodiments, electrical cables carrying information extracted from the cameras may be connected to holder body 430 adapted to wireless connects with optical gear located at the distal end 450.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:

1. A medical imaging device, comprising:
a handle adapted to operate and maneuver the medical imaging device;
an elongated rigid shaft connected to the handle, and
an extendible sleeve configured to cover at least a portion of the elongated rigid shaft, said extendible sleeve comprises
a rigid section comprising at least one optical gear, and
an extendible section, wherein extending the extendible section pushes the rigid section along a longitudinal axis of the elongated rigid shaft, and wherein sliding the rigid section over the elongated shaft changes the at least one optical gear field of view to provide a different linear field of view in an object space;
wherein the at least one optical gear on the rigid section (236) of the extendible sleeve is located at a distal tip of said extendible sleeve, and comprises a front optical gear (270, 370) and a side optical gear (275, 375, 452)
wherein each of the at least one optical gear comprises a sensor, lenses and light sources, wherein the extendible section (235) of the extendible sleeve (230) is defined by a proximal connector (212) and a distal connector (215), such that the proximal connector (212) is affixed to a distal surface of a front end (211) of the handle (210) and the distal connector (215) connects the extendible section to the rigid section, and
wherein extending the extendible section changes a distance (LS) between the distal tip of said extendible sleeve relative to a distal tip of the elongated rigid shaft, and enables the rigid section (236) to slide over the elongated rigid shaft (220) without changing the orientation of the elongated rigid shaft (220) relatively to a region of interest, wherein all of the at least one optical gear are fully contained inside the distal tip of said extendible sleeve at a collapse state and at an extended state of the extendible section (235) of the extendible sleeve (230) and during entire change of the extending.

2. The medical imaging device of claim 1, wherein the extendible section is of accordion like shape.

3. The medical imaging device of claim 1, wherein the extendible section of the extendible sleeve is made of disposable materials.

4. The medical imaging device of claim 1, wherein the extendible sleeve covers a distal end of the elongated rigid shaft.

5. The medical imaging device of claim 1, further comprises a control unit on the handle, wherein the control unit controls extension and collapse of the extendible section of the extendible sleeve.

6. The medical imaging device of claim 1, wherein when the extendible section of the sleeve has a collapse state and an extended state, wherein when in extended state, the distal tip of the extendible sleeve is distant from the distal tip of the elongated rigid shaft.

* * * * *